United States Patent [19]

Lesur et al.

[11] Patent Number: 5,859,053
[45] Date of Patent: Jan. 12, 1999

[54] ACETYLSALICYLIC ACID NITRATES

[75] Inventors: Eva Lesur, Köln; Dieter Neuser, Langenfeld; Oswald Lockhoff, Leverkusen; Elisabeth Perzborn, Wuppertal; Peter Kurka, Langenfeld; Johannes Peter Stasch, Solingen, all of Germany

[73] Assignee: Bayer Aktiengesellschaft, Leverkusen, Germany

[21] Appl. No.: 945,511

[22] PCT Filed: Apr. 19, 1996

[86] PCT No.: PCT/EP96/01630

§ 371 Date: Oct. 24, 1997

§ 102(e) Date: Oct. 24, 1997

[87] PCT Pub. No.: WO96/34848

PCT Pub. Date: Nov. 7, 1996

[30] Foreign Application Priority Data

May 2, 1995 [DE] Germany ................ 195 15 970 .5

[51] Int. Cl.$^6$ ............ A61K 31/21; C07C 203/00; C07C 69/76; C07C 233/00
[52] U.S. Cl. ............ 514/509; 558/488; 560/64; 564/169
[58] Field of Search ............ 558/488; 560/64; 564/169; 514/509

*Primary Examiner*—Johann Richter
*Assistant Examiner*—Joseph Murray
*Attorney, Agent, or Firm*—Sprung Kramer Schaefer & Briscoe

[57] ABSTRACT

The invention relates to new derivatives of acetylsalicylic acid (called ASA in the following), which contain an $NO_3$ structure. They are therapeutically active either as the intact active compound molecule or after cleavage (NO release). The invention also relates to processes for their preparation and their use as medicaments, in particular for the alleviation of pain, inhibition of platelet aggregation, lowering of fever and for the prevention of cardiovascular disorders and oncoses.

5 Claims, No Drawings

ACETYLSALICYLIC ACID NITRATES

The invention relates to new derivatives of acetylsalicylic acid (called ASA in the following), which contain an $NO_3$ structure. They are therapeutically active either as the intact active compound molecule or after cleavage (NO release). The invention also relates to processes for their preparation and their use as medicaments, in particular for the alleviation of pain, inhibition of platelet aggregation, lowering of fever and for the prevention of cardiovascular disorders and oncoses.

The valuable therapeutic effects of ASA have been known for a long time. Thus ASA is employed for the alleviation of pain, in thromboembolic disorders such as, for example, primary and secondary prevention of cardiovascular disorders, cerebrovascular disorders and peripheral vascular occlusions and also in the prevention of oncoses. In particular in the preventive indications, combinations with vitamins or other active compounds such as, for example, phytopharmaceuticals such as Ginkgo or calcium antagonists such as nifedipine, nimodipine or amlodipine are frequently employed advantageously.

Besides the valuable therapeutic effects, however, the undesired side effects of ASA, in particular on chronic administration and in high doses, have also been known for a long time. It has been attempted again and again to avoid or to decrease these undesired properties, in particular the gastrointestinal side effects, by derivatization or by means of enteric-coated administration forms. The success of these experiments to improve the tolerability of ASA, however, has until now only been seen to a small extent. One reason for this is that the lesions of the gastrointestinal mucous membrane are caused not only by the active compound directly released in this area, but also as a result of the principle of action of ASA. One cause of these undesired side effects is the inhibition of prostaglandin synthesis by ASA. There has therefore been the need for a long time to decrease the undesired side effects of ASA whilst if possible retaining the desired therapeutic effects.

It has been found that nitrates of ASA (in the following called NO-ASA) have at least the same therapeutic effects as ASA, but are virtually free of the mentioned undesired gastrointestinal side effects.

The invention relates to new NO-ASA compounds of the general formula

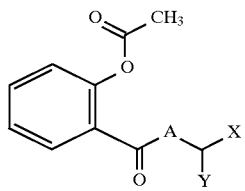

in which
A represents O or NH,
X represents $(CHZ)_m$—$CH_2$—Z,
Y represents H or $(CHZ)_n$—$CH_2$—Z, or
X and Y together represent —$(CHZ)_p$—, where
Z represents H, OH and/or $ONO_2$,
m represents a number from 1 to 4,
n represents a number from 0 to 3, and
p represents a number from 2 to 6,
with the proviso that in the compounds according to the invention at least two of the substituents Z represent $ONO_2$ or else $ONO_2$ in combination with OH.

The compounds of the formula (I) can contain one or more chiral carbon atoms and exist as optically pure compounds or as enantiomer mixtures or diastereomer mixtures.

The compounds of the general formula (I) can be prepared by reacting derivatives of ASA of the general formula (I), in which
A, X, Y, m, n and p have the meanings indicated above and
Z represents H or OH,
with concentrated nitric acid, either in pure form or as a mixture with other inorganic or organic acids, the individual hydroxyl groups being either exhaustively or partially esterified.

The reaction of alcohols with nitric acid to give nitrate esters is known. Methods for the preparation of nitric acid esters of di- or polyhydric alcohols are likewise known and described, for example, in "Methoden der organischen Chemie" [Methods of Organic Chemistry], Volume 6/2, p. 329 ff.

The compounds of the general formula (I) in which
A, X, Y, m, n and p have the meanings indicated above and
Z represents H or OH,
can be prepared from ASA or from functional derivatives of ASA, for example acid halides or mixed anhydrides of the general formula (II)

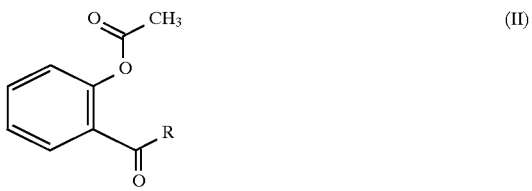

in which
R represents halogen, alkoxycarbonyloxy or optionally substituted aryloxycarbonyloxy,
by reaction with compounds of the general formula (III)

in which
A represents O or NH,
X represents $(CHZ)_m$—$CH_2$—Z,
Y represents H or $(CHZ)_n$—$CH_2$—Z, or
X and Y together represent —$(CHZ)_p$—, where
Z represents H, OH or OT,
m, n and p have the meanings indicated above and
T represents a protective group for hydroxyl functions,
followed by one or more steps for cleavage of the protective groups T with liberation of the hydroxyl function.

Suitable protective groups T are those which can be removed selectively in the presence of other carboxylic acid ester groups or carboxamide groups. Examples of such protective groups are known (P. J. Kocienski: Protecting Groups, Thieme, Stuttgart, 1994), e.g. ester groups such as 2,2,2-trichloroacetyl or ethers such as allyl, benzyl or p-methoxybenzyl or acetals such as methoxymethyl or isopropylidene, cyclohexylidene or benzylidene.

A suitable acid halide is, for example, 2-acetoxybenzoyl chloride, whose preparation is known (Riegel and Wittcoff, J. Amer. Chem. Soc., 64 (1942) 1486). Mixed anhydrides of ASA are formed in the reaction of ASA with alkoxycarbonyl halides in the presence of inorganic or organic bases, as is likewise known (Organikum, 17th Edition, Berlin 1988).

Examples of suitable alcohols of the general formula (III) are 2,2-dimethyl-4-hydroxymethyl-1,3-dioxolane or (1,4-dioxa-spiro[4,5]dec-2-yl)-methanol. Examples of suitable amines of the general formula (III) are 2,2-dimethyl-4-aminomethyl-1,3-dioxolane or (1,4-dioxa-spiro[4,5]dec-2-ylmethyl)amine.

The reactions of the compounds of the general formula (II) with those of the general formula (III) to give compounds of the general formula (IV)

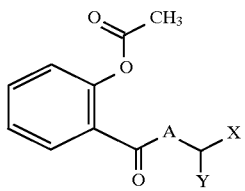  (IV)

in which
A represents O or NH,
X represents $(CHZ)_m$—$CH_2$—Z,
Y represents H or $(CHZ)_n$—$CH_2$—Z or
X and Y together represent —$(CHZ)_p$—, where
Z represents H, OH or OT,

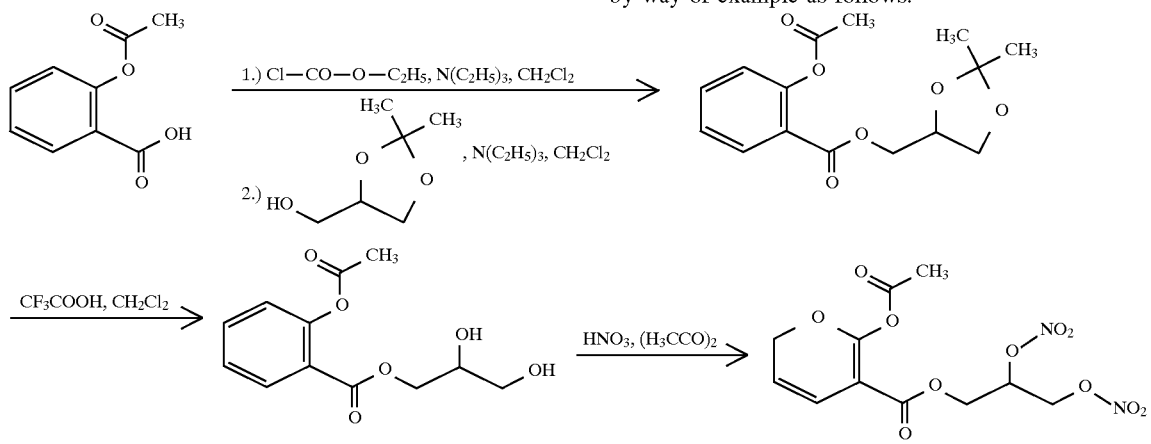

m, n and p have the meanings indicated above and
T represents a protective group for hydroxyl functions, can be carried out by known reactions of organic chemistry. In the cases in which A represents oxygen, the conditions of an alcoholysis of carboxylic acid halides or carboxylic acid anhydrides are preferably used. The reactions are preferably carried out in an organic base, for example pyridine or triethylamine, either in pure form or as a mixture with an inert organic solvent, e.g. dichloromethane, tetrahydrofuran or ethyl acetate. Suitable reaction conditions are known (Organikum, 17th Edition, p. 402 ff Berlin 1988).

In the cases in which A represents NH, the conditions of an aminolysis of carboxylic acid halides or carboxylic acid anhydrides are preferably used. The reaction is preferably carried out in organic solvents, such as simple alcohols, dichloromethane or tetrahydrofuran, if appropriate in the presence of an organic base. Suitable reaction conditions are known (Organikum, 17th Edition, p. 408 ff Berlin 1988).

Conditions for the removal of the protective groups T are known and are indicated, for example, in P. J. Kocienski: Protecting Groups, Thieme-Verlag, Stuttgart, 1994.

The compounds of the general formula (IV) in which A represents oxygen and X, Y, Z, T, m, n and p have the meanings indicated above, can also be prepared from alkali metal salts of ASA by reaction of compounds of the general formula (V)

 (V)

in which
U represents halogen, p-toluenesulphonyl, methylsulphonyl or trifluoromethylsulphonyl,
X represents $(CHZ)_m$—$CH_2$—Z,
Y represents H or $(CHZ)_n$—$CH_2$—Z, or
X and Y together represent —$(CHZ)_p$—, where
Z represents H, OH or OT,
m, n and p have the meanings indicated above and
T represents a protective group for hydroxyl functions.

The reactions can be carried out in dipolar aprotic solvents, for example hexamethylphosphoramide, at room temperature (see: Parker, Adv. Org. Chem., 5 (1965) 1-46 or Alvarez and Watt, J. Org. Chem., 33 (1968) 2143).

The process according to the invention for the preparation of the compounds of the general formula (I) can be shown by way of example as follows:

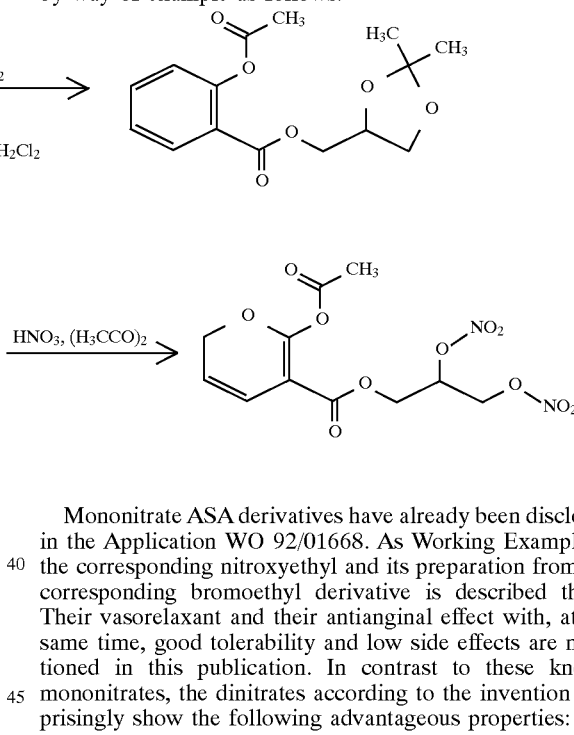

Mononitrate ASA derivatives have already been disclosed in the Application WO 92/01668. As Working Example 8, the corresponding nitroxyethyl and its preparation from the corresponding bromoethyl derivative is described there. Their vasorelaxant and their antianginal effect with, at the same time, good tolerability and low side effects are mentioned in this publication. In contrast to these known mononitrates, the dinitrates according to the invention surprisingly show the following advantageous properties:

1. The inhibition of platelet aggregation is more strongly marked with the nitrates according to the invention than with the known mononitrates.
2. The tolerability of the nitrates according to the invention is at least just as good as that of the mononitrates and markedly increased compared with native aspirin.

The present invention likewise relates to pharmaceutical preparations comprising NO-ASA compounds of the general formula (I) in addition to customary auxiliaries and excipients, e.g. in the form of tablets, coated tablets, capsules or solutions, preferably for oral administration. Besides the new active compound of the general formula (I), these preparations can also contain other pharmaceutical active compounds such as, for example, vitamins such as A, B, C or E or β-carotene, phytopharmaceuticals such as, for example, Ginkgo extracts or calcium antagonists, in particular from the dihydropyridines group, such as, for example, nifedipine, nitrendipine, nimodipine, felodipine, nicardipine or amlodipine.

These pharmaceutical preparations are prepared by customary methods. As a result of the improved tolerability and the additional effect of the NO derivatives, hitherto customary ASA doses can be reduced to achieve the same effect or, in the case of chronic administration, the treatment time can be extended and thus the therapeutic success increased.

WORKING EXAMPLES

Example 1 a) 2,2-Dimethyl-[1,3]dioxolan-4-yl-methyl 2-acetoxybenzoate

The solution from 2-acetoxybenzoic acid (10.0 g, 55.5 mmol) in dichloromethane (200 ml) is treated with triethylamine (7.7 ml, 55.5 mmol), cooled to 0° C., treated dropwise with ethyl chloroformate (5.3 ml, 55.5 mmol), stirred at 0° C. for 1 h and filtered. The filtrate is added at room temperature to a solution of (±)-2,2-dimethyl-4-hydroxymethyl-1,3-dioxolane (7.33 g, 55.5 mmol) and triethylamine (50 ml) in dichloromethane (100 ml). After 4 h, water (50 ml) is added and the mixture is stirred. The organic phase is washed with dilute hydrochloric acid, saturated aqueous sodium hydrogencarbonate solution and water, dried over magnesium sulphate and concentrated. The residue is purified by column chromatography on silica gel 60 (hexane/ethyl acetate =15/1). Yield: 8.4 g.

$C_{15}H_{18}O_6$[294.3]. Syrup, $R_f$=0.48 (toluene/ethyl acetate=3/1).

b) 2,3-Dihydroxy-propyl 2-acetoxybenzoate

The solution from 2,2-dimethyl-[1,3]dioxolan-4-yl-methyl 2-acetoxybenzoate (5.7 g, 19.4 mmol) in dichloromethane (50 ml) is treated with trifluoroacetic acid (10 ml). After 3 h, the mixture is concentrated in vacuo, the residue is taken up in toluene (30 ml) and the solution is concentrated. The residue is purified by flash chromatography (gradient hexane/ethyl acetate=3/1→2/1 →1/1). Yield: 2.96 g.

$C_{12}H_{14}O_6$[254.2]. Syrup, $R_f$=0.19 (dichloromethane/methanol=15/1).

c) 2,3-Bisnitrooxy-propyl 2-acetoxybenzoate

The solution from 2,3-dihydroxy-propyl 2-acetoxybenzoate (1.0 g, 3.93 mmol) in acetic anhydride (10 ml) is treated dropwise at –10° C. with a cooled solution of acetic anhydride (10 ml) and nitric acid (98%; 8 ml). After 30 min, the mixture is poured onto ice, treated with dichloromethane (100 ml) and stirred for 20 min. The organic phase is washed with saturated aqueous sodium hydrogencarbonate solution and water, dried over magnesium sulphate and concentrated. The residue is purified by column chromatography on silica gel 60 (hexane-ethyl acetate=10/1). Yield: 1.01 g.

$C_{12}H_{12}N_2O_{10}$[344.2]. Syrup, $R_f$=0.77 (hexane/ethyl acetate=1/1). CI—MS: m/e 345 (M+H$^+$). $^1$H—NMR (500 MHz, CDCl$_3$):δ=7.97, 7.62, 7.35, 7.14 (4×1 H, aromatic), 5.57 (m, 1 H, H-2), 4.89 (dd, 1 H, H-3a), 4.63 (dd, 1 H, H-3b), 4.64 (ddd, 1 H, H-la), 4.51 (ddd, 1 H, H-1b), 2.36 (s, 3 H, Ac).

Example 2 a) [2S]-1,4-Dioxa-spiro[4,5]dec-2-yl-methyl trifluoromethanesulphonate

The solution from [2R]-1,4-dioxa-spiro[4,5]dec-2-yl-methanol (1.0 g, 5.8 mmol) in dichloromethane (4 ml) and pyridine (4 ml) is treated at –20° C. with a solution of trifluoromethanesulphonic anhydride (1.9 ml, 11.6 mmol) in dichloromethane (10 ml). After 1 h at –10° C., the mixture is poured onto ice water. Dichloromethane (20 ml) is added. The organic phase is washed with dilute hydrochloric acid, saturated aqueous sodium hydrogencarbonate solution and water, dried over magnesium sulphate and concentrated. The residue is employed in the following reaction without further purification. Yield: 1.27 g.

$C_{16}H_{15}F_3O_5S$[303.2]. Syrup, $R_f$=0.66 (toluene/ethyl acetate=3/1).

b) [2S]-1,4-Dioxa-spiro-[4,5]dec-2-yl-methyl 2-acetoxybenzoate

The solution from 2-acetoxy-benzoic acid (0.6 g, 3.33 mmol) in ethanol (3.5 ml) is treated with a solution of caesium carbonate (0.54 g, 1.67 mmol) in water (35 ml) and stirred. After 30 min, the mixture is freeze-dried. The residue is added with stirring to a solution of [2S]-1,4-dioxa-spiro [4,5]dec-2-yl-methyl trifluoromethanesulphonate (1.15 g, 3.79 mmol) in N,N-dimethylformamide (10 ml). After 16 h at 20° C., the mixture is concentrated, the residue is taken up in dichloromethane (50 ml), and the solution is washed twice with water, dried over magnesium sulphate and concentrated. The residue is purified by column chromatography (toluene/ethyl acetate=50/1). Yield: 601 mg.

$C_{18}H_{22}O_6$[334.4]. Syrup, $R_f$=0.35 (toluene/ethyl acetate=10/1)

c) [2S]-2,3-dihydroxy-propyl 2-acetoxybenzoate

The solution from [2S]-1,4-dioxa-spiro[4,5]dec-2-yl-methyl 2-acetoxybenzoate (527 mg, 1.58 mmol) in dichloromethane (10 ml) is treated with trifluoroacetic acid (2 ml). After 2 h at room temperature, the mixture is concentrated, the residue is taken up in toluene (10 ml) and the solution is concentrated. The residue is purified by column chromatography (dichloromethane/methanol=30/1). Yield: 161 mg.

$C_{12}H_{14}O_6$[254.2]. Syrup, $R_f$=0.15 (dichloromethane/methanol=10/1).

d) [2S]-2,3-bisnitrooxy-propyl 2-acetoxybenzoate

The solution from [2S]-2,3-dihydroxy-propyl 2-acetoxybenzoate (50 mg, 0.20 mmol) in acetic anhydride (0.5 ml) is treated dropwise at –10° C. with a cooled solution of acetic anhydride (0.5 ml) and nitric acid (98%; 0.4 ml). After 30 min, the mixture is poured onto ice, treated with dichloromethane (5 ml) and stirred for 20 min. The organic phase is washed with saturated aqueous sodium hydrogencarbonate solution and water, dried over magnesium sulphate and concentrated. The residue is purified by column chromatography on silica gel 60 (hexane/ethyl acetate=10/1). Yield: 34 mg.

$C_{12}H_{12}N_2O_{10}$[344.2]. Syrup, $R_f$=0.48 (hexane/ethyl acetate=2/1), [α]$_D$=+0.8° (c=0.20, dichloromethane). CI-MS: m/e345(M+H$^+$). $^1$H—NMR (500 MHz, CDCl$_3$): δ=7.97, 7.62, 7.35, 7.14 (4×1 H, aromatic), 5.57 (m, 1 H, H-2), 4.89 (dd, 1 H, H-3a), 4.63 (dd, 1 H, H-3b), 4.64 (ddd, 1 H, H-la), 4.51 (ddd, 1 H, H-1b), 2.36 (s, 3 H, Ac).

Example 3 a) 2-Acetoxybenzoic acid 2,2-dimethyl-[1,3]dioxolan-4-yl-methylamide

The solution from 2-acetoxybenzoic acid (216 mg, 1.2 mmol) in dichloromethane (4 ml) is treated with triethylamine (0.15 ml, 1.2 mmol), cooled to 0° C., treated dropwise with ethyl chloroformate (0.144 ml, 1.0 mmol), stirred at 0° C. for 2 h and filtered. The filtrate is added at room temperature to a solution of 2,2-dimethyl-4-aminomethyl-1,3-dioxolane (293 mg, 1.0 mmol) and triethylamine (0.14 ml) in dichloromethane (4 ml). After 4 h, water (10 ml) is added and the mixture is stirred. The organic phase is washed with dilute hydrochloric acid, saturated aqueous sodium hydrogencarbonate solution and water, dried over magnesium sulphate and concentrated. The residue is purified by column chromatography on silica gel 60 (gradient hexane/ethyl acetate=3/1→1/1). Yield: 143 mg.

$C_{15}H_{19}NO_5$ [293.3]. Syrup, $R_f$=0.1 (hexane/ethyl acetate=2/1)

b) 2-Acetoxybenzoic acid 2,3-dihydroxy-propylamide

The solution from 2-acetoxybenzoic acid 2,2-dimethyl-[1,3]dioxolan-4-yl-methylamide (184 mg, 0.63 mmol) in dichloromethane (5 ml) is treated with trifluoroacetic acid (1 ml). After 0.5 h at room temperature, the mixture is concentrated, the residue is taken up in toluene (10 ml) and the solution is concentrated. The residue is purified by column chromatography (dichloromethane/methanol=10/1). Yield: 132 mg.

$C_{12}H_{15}NO_5$ [253.2]. Syrup, $R_f$=0.17 (dichloromethane/methanol=10/1).

c) 2-Acetoxybenzoic acid 2,3-bisnitrooxy-propylamide

The solution from 2-acetoxybenzoic acid 2,3-dihydroxy-propylamide (50 mg, 0.20 mmol) in acetic anhydride (0.5 ml) is treated dropwise at −10° C. with a cooled solution of acetic anhydride (0.5 ml) and nitric acid (98%; 0.4 ml). After 30 min, the mixture is poured onto ice, treated with dichloromethane (5 ml) and stirred for 20 min. The organic phase is washed with saturated aqueous sodium hydrogencarbonate solution and water, dried over magnesium sulphate and concentrated. The residue is purified by column chromatography on silica gel 60 (hexane/ethyl acetate=13/1). Yield: 29 mg.

$C_{12}H_{13}N_3O_9$ [343.2]. Syrup, $R_f$=0.36 (hexane/ethyl acetate=1/1). CI-MS: m/e 344 (M+H$^+$). $^1$H—NMR (400 MHz, CDCl$_3$):δ=7.75, 7.53, 7.32, 7.14 (4×1 H, aromatic), 6.64 (m, 1 H, NH), 5.52 (m, 1 H, H-2), 4.95 (dd, 1 H, H-3a), 4.60 (dd, 1 H, H-3b), 3.85 (ddd, 1 H, H-1a), 3.76 (ddd, 1 H, H-1b), 2.37 (s, 3 H, Ac).

The following were prepared by analogous processes:

4. 2,3,4-Trisnitrooxy-butyl 2-acetoxybenzoate
5. 2-Nitrooxy-1-nitroxymethyl-ethyl 2-acetoxybenzoate
6. 2-Hydroxy-3-nitrooxy-1-nitrooxymethyl-propyl 2-acetoxybenzoate
7. 2,3-Bisnitrooxy-1-nitrooxymethyl-propyl 2-acetoxybenzoate
8. 3,4-Bisnitrooxy-cyclohexyl 2-acetoxybenzoate Pharmaceutical working examples

| Example 1 (rapid-release effervescent tablets) | |
|---|---|
| NO-ASA | 100 mg |
| Sodium citrate, primary | 1306 mg |
| Citric acid, powder | 260 mg |
| Sodium hydrogencarbonate | 484 mg |
| Sodium carbonate | 200 mg |
| Total weight | 2350 mg |

Preparation:

NO-ASA, sodium citrate and citric acid are granulated with water in a fluidized bed, dried and sieved. The particle size of the granules is preferably to 90% between 125 and 400 μm. The remaining constituents (Na hydrogencarbonate, Na carbonate) are admixed to these granules under suitable climatic conditions and this mixture is compressed in suitable tablet presses to give effervescent tablets having a diameter of 20 mm. The tablets are then packed, e.g. in aluminium/aluminium blister packs.

Examples 2, 3 and 4 are prepared analogously to Example 1.

| Example 2 (rapid-release effervescent tablets) | |
|---|---|
| NO-ASA | 500 mg |
| Sodium citrate, primary | 1306 mg |
| Citric acid, powder | 260 mg |
| Sodium hydrogencarbonate | 484 mg |
| Sodium carbonate | 200 mg |
| Total weight | 2750 mg |

| Example 3 (rapid-release effervescent tablets) | |
|---|---|
| NO-ASA | 100 mg |
| Amlodipine | 10 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 μg |
| Nicotinamide | 100 mg |
| Ascorbic acid | 200 mg |
| D-α-Tocopherol acetate | 15 mg |
| Dry extract of Ginkgo biloba leaves (50:1), standardized to 960 mg of Ginkgo flavone glycosides and 240 mg of terpene lactones | 40 mg |
| Sodium citrate, primary | 1306 mg |
| Citric acid, powder | 260 mg |
| Sodium hydrogencarbonate | 483 mg |
| Sodium carbonate | 200 mg |
| Total weight | 2740 mg |

| Example 4 (rapid-release effervescent tablets) | |
|---|---|
| NO-ASA | 500 mg |
| Nifedipine | 90 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 μg |
| Nicotinamide | 100 mg |
| Ascorbic acid | 200 mg |
| D-α-Tocopherol acetate | 15 mg |
| Dry extract of Ginkgo biloba leaves (50:1), standardized to 960 mg of Ginkgo flavone glycosides and 240 mg of terpene lactones | 40 mg |
| Sodium citrate, primary | 1306 mg |
| Citric acid, powder | 260 mg |
| Sodium hydrogencarbonate | 483 mg |
| Sodium carbonate | 200 mg |
| Total weight | 3220 mg |

| Example 5 (delayed-release tablets) | |
|---|---|
| NO-ASA | 100 mg |
| Metholose 60 SH 50 | 398.5 mg |
| Mg stearate | 1.5 mg |
| Total weight | 500 mg |

Preparation:

NO-ASA is homogeneously mixed with Metholose 60SH50 and then dry-compacted on suitable rolls. The scales formed in this way are broken in a compactor with the aid of a suitable sieve to give granules having a particle size distribution preferably of between 63 and 400 μm. The granules are mixed with magnesium stearate, compressed to give tablets and then packed, e.g. in aluminium/aluminium blister packs. Example 6 is prepared analogously.

| Example 6 (delayed-release tablets) | |
|---|---|
| NO-ASA | 100 mg |
| Nifedipine | 30 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 μg |
| Nicotinamide | 100 mg |
| Ascorbic acid | 200 mg |
| D-α-Tocopherol acetate | 15 mg |
| Dry extract of Ginkgo biloba leaves (50:1), standardized to 960 mg of Ginkgo flavone glycosides and 240 mg of terpene lactones | 40 mg |
| Metholose 60 SH 50 | 400 mg |
| Mg stearate | 4 mg |
| Total weight | 915 mg |

We claim:

1. Compounds of the general formula (I)

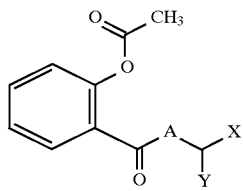

(I)

in which

A represents O or NH,

X represents $(CHZ)_m$—$CH_2$—Z,

Y represents H or $(CHZ)_n$—$CH_2$—Z, or

X and Y together represent —$(CHZ)_p$—, where

Z represents H, OH and/or $ONO_2$, m represents a number from 1 to 4, n represents a number from 0 to 3, and p represents a number from 2 to 6, with the proviso that in the compounds according to the invention at least two of the substituents Z represent $ONO_2$ or else $ONO_2$ in combination with OH.

2. Process for the preparation of compounds of the general formula (I) according to claim 1, wherein derivatives of ASA of the general formula (I), in which A, X, Y, m, n and p have the meanings indicated above and Z represents H or OH, are reacted with concentrated nitric acid, either in pure form or as a mixture with other inorganic or organic acids, the individual hydroxyl groups being either exhaustively or partially esterified.

3. A composition comprising at least one compound of the general formula (I), as an active ingredient, according to claim 1.

4. Compounds of the general formula (I) according to claim 1, in which

A, X, Y, m, n and p have the meaning indicated in claim 1 and

Z represents hydrogen or hydroxyl.

5. Process for the preparation of compounds of the general formula (I) according to claim 4, wherein ASA derivatives of the general formula (II)

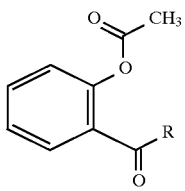

(II)

in which

R represents halogen, alkoxycarbonyloxy or optionally substituted aryloxycarbonyloxy, are reacted with compounds of the general formula (III)

(III)

in which

A represents O or NH,

X represents $(CHZ)_m$—$CH_2$—Z,

Y represents H or $(CHZ)_n$—$CH_2$—Z, or

X and Y together represent —$(CHZ)_p$—, where

Z represents H, OH or OT, m, n and p have the meanings indicated above and

T represents a protective group for hydroxyl functions, and in one or more steps the protective groups T are removed with liberation of the hydroxyl function.

* * * * *

UNITED STATES PATENT AND TRADEMARK OFFICE
CERTIFICATE OF CORRECTION

PATENT NO. : 5,859,053
DATED : January 12, 1999
INVENTOR(S) : Lesur et al.

It is certified that error appears in the above-identified patent and that said Letters Patent is hereby corrected as shown below:

Title Page        Insert --REFERENCES CITED
                     U.S. PATENT DOCUMENTS
         5,366,992    11/1994   Sala et al.   558,484

FOREIGN PATENT DOCUMENTS
                 WO92/01668   2/1992   World
                 WO94/03421   2/1994   World
                 WO95/30642   11/1995   World OTHER DOCUMENTS
        Methoden der organischen Chemie, Band 6/2, 329 ff.
         Kocienski, Protecting Groups, Thieme, Stutgart (1994).
   Riegel und Witcoff, J. Amer. Chem. Soc. 64 (1942) 1486.
      Organikum, 17. Aufl., S. 402 ff, Berlin 1988.
      Organikum, 17. Aufl., S. 408 ff, Berlin 1988.
      Parker, Adv. Org. Chem. 5 (1965) 1-46.
      Alvarez and Watt, J. Org. Chem. 33 (1968) 2143. --

Signed and Sealed this

Twenty-eighth Day of March, 2000

Attest:

Q. TODD DICKINSON

*Attesting Officer*          *Commissioner of Patents and Trademarks*